United States Patent
Frey

Patent Number: 6,036,671
Date of Patent: Mar. 14, 2000

[54] BREAKAWAY SYRINGE AND DISPOSAL APPARATUS

[76] Inventor: William J. Frey, 25111 Nueva Vista, Laguna Niguel, Calif. 92677

[21] Appl. No.: 08/895,761

[22] Filed: Jul. 17, 1997

[51] Int. Cl.$^7$ ..................................................... A61M 5/00
[52] U.S. Cl. ........................... 604/110; 604/263; 206/364
[58] Field of Search .................................... 604/110, 187, 604/192, 263; 206/364, 365

[56] References Cited

U.S. PATENT DOCUMENTS

| | | |
|---|---|---|
| 1,599,881 | 9/1926 | Eisele . |
| 2,929,510 | 3/1960 | Penn . |
| 3,320,954 | 5/1967 | Cowley ..................................... 604/110 |
| 4,010,756 | 3/1977 | DuMont et al. . |
| 4,121,588 | 10/1978 | Geiger . |
| 4,220,151 | 9/1980 | Whitney ................................... 604/110 |
| 4,540,405 | 9/1985 | Miller et al. . |
| 4,786,280 | 11/1988 | Maeda ..................................... 604/110 |
| 4,875,265 | 10/1989 | Yoshida . |
| 4,883,173 | 11/1989 | Goldman et al. . |
| 4,892,191 | 1/1990 | Nakamura . |
| 4,989,307 | 2/1991 | Sharpe et al. . |
| 4,995,871 | 2/1991 | Sasaki et al. ............................ 604/110 |
| 5,067,223 | 11/1991 | Bruno . |
| 5,112,315 | 5/1992 | Gloyer et al. . |
| 5,127,522 | 7/1992 | Ranford . |
| 5,187,850 | 2/1993 | McCammon et al. ................... 604/110 |
| 5,201,720 | 4/1993 | Borgia et al. . |
| 5,222,944 | 6/1993 | Harris . |
| 5,242,419 | 9/1993 | Kiner et al. . |
| 5,279,580 | 1/1994 | Wallingford . |
| 5,318,537 | 6/1994 | Van Der Merwe ..................... 604/110 |
| 5,338,304 | 8/1994 | Adams . |
| 5,347,078 | 9/1994 | Eckels . |
| 5,380,296 | 1/1995 | Smedley et al. . |
| 5,409,113 | 4/1995 | Richardson et al. . |
| 5,417,659 | 5/1995 | Gaba . |
| 5,431,631 | 7/1995 | Lu . |
| 5,501,670 | 3/1996 | Sak . |
| 5,637,099 | 6/1997 | Durdin et al. .......................... 604/192 |

FOREIGN PATENT DOCUMENTS

| | | | |
|---|---|---|---|
| 304619 | 3/1989 | European Pat. Off. ............... | 604/192 |
| 2646609 | 11/1990 | France ................................... | 604/110 |
| 2662363 | 11/1991 | France ................................... | 604/110 |

OTHER PUBLICATIONS

Abstract for U.S. Patent No. 5,508,681; Interactive Safe for Disposal of Medical Needles; dated Apr. 24, 1996; 2 pages.
Abstract for U.S. Patent No. 5,507,041; Needle Holding Apparatus and Method of Use; dated Apr. 24, 1996; 2 pages.

*Primary Examiner*—John D. Yasko
*Attorney, Agent, or Firm*—Richard L. Myers

[57] ABSTRACT

A breakaway intravenous needle device, including a syringe and needle assembly, and a disposal apparatus for removing, retaining and discarding needles attached to the intravenous needle device. The breakaway syringe comprises a syringe barrel which extends from a proximal barrel end to a distal barrel end. A nozzle extends distally from the distal barrel end and includes a weakened portion. Bending of the syringe barrel relative to the nozzle distal end causes the syringe to break along the weakened portion. When coupled with a needle hub and needle assembly and used with the disposal apparatus of the present invention, the syringe and attached needle assembly are held stationary within an aperture disposed on the disposal apparatus. The syringe barrel may then be moved laterally or otherwise bent relative to the needle hub to break the syringe along the weakened portion of the nozzle. The needle hub and needle assembly, now broken away from the remainder of the syringe fall freely into the disposal apparatus. A locking mechanism is provided within the aperture to prevent the removal of the needle hub and attached needle assembly once inserted within the disposal apparatus. A cover is also disclosed to facilitate the bending and breaking of the syringe relative to the needle hub and needle assembly and to provide additional user protection.

23 Claims, 4 Drawing Sheets

BREAKAWAY SYRINGE AND DISPOSAL APPARATUS

FIELD OF THE INVENTION

This invention relates generally to intravenous needle devices and needle disposal containers and more particularly, to an intravenous needle device having a breakaway feature and an associated container for safely breaking away and retaining a needle assembly coupled with the intravenous needle device.

BACKGROUND OF THE INVENTION

The disposal of hypodermic needles and their associated attached device has become of greater importance in recent years because of the spread of various blood transmitted diseases. In particular, percutaneous injuries by such needles have presented a serious problem. Diseases such as hepatitis and AIDS are known to be transmitted through blood and by needle stick injuries. Recently, an even greater danger has been recognized in connection with the handling and dismantling of used needles and other sharp medical implements. It is now recognized that certain diseases, most notably Hepatitis B, can be transmitted by merely contacting a contaminated needle or implement. Thus, the safe disposal of used needles and their associated devices, such as syringes is a major concern to users as well as health care personnel.

In order to minimize the risk of contact with a used needle as well as avoiding needle stick injuries, retractable-type syringes have been developed. These syringes enable the retraction of the needle into the barrel of the syringe following use and prior to disposal. The movement of the needle into the retracted position is typically limited such that the needle can not protrude from the barrel and thus would not normally come again into contact with another person. However, these retractable-type syringes are relatively complex and expensive. In addition, failure of a single syringe can have serious consequences. Additionally, by retracting the needle within the syringe, the needle is still potentially dangerous. For example, dropping of the syringe may break the syringe barrel exposing the needle.

In addition to safety syringe devices, a number of hypodermic needle disposal devices have been developed to allow medical personnel, as well as other users, to dispose of the entire hypodermic syringe, including the attached needle assembly. However, to be effectively used, these disposal devices must be readily accessible to the medical personal and other user so that the syringe and needle assembly may be quickly and safely disposed of promptly after use. Additionally, because a large number of syringe and needle assemblies may be used, it is important that the container be inexpensive and simple to use.

These disposal devices function by separating the needle assembly from the syringe. The needle assembly is retained within the disposal device and the now separated syringe may be disposed of using typical medical procedures. Since the needle assembly normally includes a hub which is attached to the distal end of the syringe through a threaded connection or frictional slip-fit connection, removal at this connection is relatively efficient. These needle disposal devices are available for use with both threaded and slip-fit type connections.

A typical needle assembly disposal device for use with a syringe having a removable needle assembly includes a container having a lid which includes a hole contiguous with a tapered slot to allow the needle hub to be jammed into the tapered slot. The needle assembly is then removed by manual manipulation of the syringe or the needle assembly. Similar devices for use exclusively with threaded hubs, have utilized a stair-stepped edge along the slot to engage ribs along the threaded hub in a manner similar to a hub wrench. Many of these devices disadvantageously require the use of both hands, one to hold the body of the device or disposal container steady, and the other to position the hub of the medical unit in the hole, engage it in the converging slot, and rotate the barrel of the syringe to remove the hub and needle assembly.

Many of these needle disposal devices incorporate large openings in their lids. These openings may be used for insertion of the needle assembly as well as for a mini medical waste receptacle. Such openings compromise the protection offered by these units by allowing a finger or other object to extend into the container holding the contaminated needles, thus increasing the risk of personal injury. Also, if the disposal container is not secured in place, it may be tipped or knocked over, allowing the used needles and any contaminated material to spill from the opening in the disposal container. This presents another potential hazard of skin contact or even punctures by the used needles.

Another disadvantage of these needle disposal devices occurs after the needle is inserted into the opening. Often times medical personnel or others users will merely insert the syringe and attached needle assembly into the opening in the disposal device without removing or otherwise detaching the needle assembly. This leaves the syringe end extending out from the disposal device. When a second syringe and needle assembly requires disposal, the first syringe inserted into the disposal device must be removed prior to insertion of the second device. The user must thus, remove the first syringe from the disposal device without knowing whether the needle is still attached or was previously removed. This may potentially expose the first needle. In addition, this requires additional handling of the second syringe and needle assembly. Thus, there is a need for a needle disposal device which prevents the removal of the needle assembly after insertion. This also prevents the potential re-use of the syringe and needle assembly.

Another disadvantage of the present needle disposal devices occurs when the needle hub is inserted within the opening of the disposal device. Since the needle hub is firmly captured between the sidewalls of the opening when the syringe is turned or otherwise manipulated, the needle hub tends to remain captured within the opening walls without falling into the device container. The medical personnel or other user must now clear the opening in the device which prevents the potential for contact with contaminated fluid or even direct injury.

SUMMARY OF THE INVENTION

The present invention overcomes these problems of the past by providing a syringe having a nozzle incorporating a weakened portion which functions as a breakaway. The breakaway feature allows a distal portion of the syringe nozzle and an attached needle assembly to be broken away from the syringe barrel and discarded. The breakaway feature also prevents any possible reuse of the syringe as well as the needle assembly. For purposes of this disclosure, the term "syringe" shall include all types of intravenous syringes, intravenous accesses and stylets, and any other intravenous device which incorporated a needle assembly.

The present invention also satisfies the need for a disposal container which can safely receive and dispose of used or contaminated needle assemblies. When used in conjunction with a syringe having a breakaway feature, the disposal container facilitates the removal of the needle assembly and the lower portion of the syringe nozzle without concern for injury or contact with the needle by medical personnel or other users. By providing the syringe with the breakaway feature adjacent the needle hub assembly, the amount of waste inserted into the disposal container is minimized.

The present invention is generally directed to a syringe for coupling with a needle assembly. The syringe includes a tubular syringe barrel which extends along a longitudinal axis between a proximal barrel end and a distal barrel end. A nozzle having a nozzle passageway extending from a nozzle proximal end to a nozzle distal end is coupled to the distal barrel end. Particularly, the nozzle proximal end extends from the distal barrel end along the longitudinal axis to nozzle distal end. The nozzle passageway is fluidly connected to the syringe barrel. A plunger is slidably disposed within the syringe barrel.

The nozzle includes a weakened portion between the nozzle proximal end and the nozzle distal end. The weakened portion may comprises an annular groove which circumscribes the nozzle or alternatively, a plurality of grooves which generally circumscribe the nozzle. The syringe, and particularly, the nozzle is breakable about the weakened portion when the syringe barrel is bent or otherwise moved laterally relative to the nozzle distal end.

A needle assembly for coupling with a needle hub may include a proximal needle end and a distal needle end. The proximal needle end is attached to the needle hub and the hub is coupled to the nozzle distal end using conventional techniques. Alternatively, the syringe may be constructed with the needle hub attached such that the syringe and hub are a single piece component. As is conventionally known, the syringe and needle assembly may be used to transfer a substance from within the syringe barrel and out of the needle distal end or alternatively, drawn through the distal needle end and into the syringe barrel.

In another aspect of the present invention a disposal apparatus is used to break and dispose of the syringe and hub and needle assembly. The disposal apparatus comprises an enclosure or container body having a base and at least one surrounding sidewall. The container body is configured for containing the hub and needle assembly and the portion of the syringe that has been broken away from the syringe barrel. An upper portion or top is attached to the container body. The upper portion encloses the disposal device but includes an aperture for receiving the needle hub and needle assembly. The aperture has a generally rigid surrounding wall for supporting the needle hub. Once the needle hub and needle assembly are fully inserted into the aperture, the syringe and attached needle assembly are fully supported by the disposal apparatus and particularly by the aperture wall.

A locking mechanism is coupled within the aperture. The locking mechanism includes a locking tip which is movable within the aperture for engaging the needle hub. The needle hub includes a proximal hub end which has a flat surface or hub and which is generally perpendicular to the longitudinal axis of the syringe. The locking tip is configured with a tapered side to allow the needle hub and needle assembly to easily slide into the aperture and a flat side configured to engage with the flat surface of the proximal hub end. The needle assembly is mechanically restrained from passing too far within the aperture by a mechanical stop on the upper portion of the container or alternatively on the syringe barrel. The mechanical stop is configured to ensure that the flat proximal portion of the needle hub moves past the locking tip. Once the needle hub and needle assembly have been fully inserted, the locking tip prevents the needle hub and attached needle assembly from being pulled or otherwise moved back out of the aperture. The disposal apparatus is thus configured such that the syringe, needle hub and attached needle assembly are generally rigidly retained within the aperture. This allows the syringe to be broken along the weakened portion when the syringe barrel is bent relative to the nozzle distal end.

In yet another aspect of the present invention, the disposal apparatus includes a second aperture for receiving a second syringe, needle hub and needle assembly. The second syringe and needle assembly are configured substantially like the first syringe and needle assembly but may be of a different size or overall shape. A second locking mechanism is incorporated within the second aperture for retaining the second syringe and needle assembly. The second locking mechanism includes a flexible arm which is connected to the upper portion of the apparatus at a first end and to a second locking tip at a second end. The second aperture within the disposal apparatus allows for the breaking and disposal of two different syringe and needle assembly sizes within one container. Alternatively, the second aperture allows for the disposal of two different types of syringes, such as a conventional intravenous syringe and an intravenous stylet.

In yet another aspect of the present invention, the disposal apparatus includes a cover for covering the aperture. The cover is pivotally connected with a pair of side walls on the upper portion of the disposal apparatus such that it may be moved to expose the aperture or closed to cover the aperture. The cover includes a syringe contact ledge for contacting the syringe barrel and for use in bending the syringe barrel relative to the needle hub fixed within the aperture. Thus, the cover may be moved to contact and break the syringe and needle assembly which has been inserted into the aperture within the container. Once broken apart from the nozzle, the syringe barrel is retained between the now closed cover, the side walls and a support ledge on the upper portion. In this position, the cover closes the aperture and prevents any material or needle assemblies from within the container from protruding. The broken away needle assembly and nozzle distal end fall freely into the container. The cover may be moved to the open position to remove the syringe barrel for its disposal and to expose the aperture for reuse with a next syringe and attached needle hub and needle assembly.

This invention, together with the additional features and advantages thereof, which is only summarized in the foregoing passages, will become more apparent to those of skill in the art upon reading the description of the preferred embodiments, which follows in the specification, taken together with the following drawings.

DESCRIPTION OF THE PREFERRED EMBODIMENTS

Figure 1:
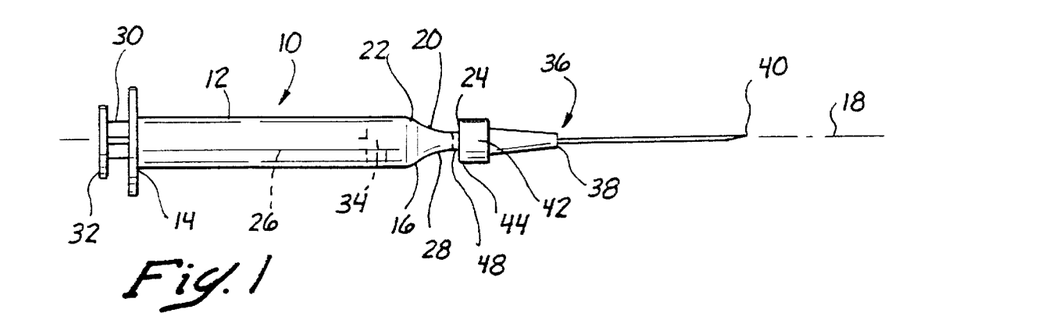
FIG. 1 is a side view of a syringe according to an embodiment of the present invention shown coupled with a needle assembly.

Referring now to the drawings, wherein like reference characters designate identical or corresponding parts throughout the several views and embodiments, a syringe according to the principles of the present invention is illustrated in FIG. 1 and designated by the reference numeral 10. As shown, the syringe 10 may include a hollow tubular body or syringe barrel 12 which extends between a proximal barrel end 14 and a distal barrel end 16 along a longitudinal axis 18. A nozzle 20 is coupled to the distal barrel end 16 at a nozzle proximal end 22 and extends along the longitudinal axis 18 to a nozzle distal end extend 24. A passageway 26 extends along the longitudinal axis 18 from the proximal barrel end 14 and through the nozzle distal end 20. The nozzle 20 may be tapered and may be an integral part of the syringe barrel 12 as is conventionally known.

A weakened portion 28 is configured about the nozzle 20 between the nozzle proximal end 22 and the nozzle distal end 24. The weakened portion 28 may also be configured at the junction of the distal barrel end 16 and the nozzle, proximal end 22. Alternatively, the weakened portion 28 may be configured around the syringe barrel 12 adjacent the distal barrel end 16. The weakened portion 28 is configured such that the syringe 10 may be broken about the weakened portion 28 when the proximal barrel end 14 is moved laterally or bent relative to the distal barrel end 16. However, the syringe 10, including the weakened portion 28, retains sufficient bending and shear strength to resist breaking about the weakened portion 28 during normal or even heavy use.

The weakened portion 28 may comprise an etching or groove which generally circumscribes the syringe 10. The annular groove or etching may also comprise a series of grooves or etches which generally circumscribe the nozzle 20. Any other method of creating a weakened portion or zone about the nozzle 20 may be used. For example, the nozzle 20 may comprise a junction, the junction may even comprise differing materials, with the junction being the weakened portion 28. As a second example, the nozzle may comprise a plurality of materials with one of the materials being more brittle to create a weakened point.

To facilitate breakage and disposal of the syringe 10, regardless of its orientation during disposal, the weakened portion 28 may include an annular groove surrounding the nozzle 20 or other weakened portion 28 location. Preferably, the annular groove is oriented such that it is generally perpendicular to the longitudinal axis 18. The depth of the annular groove, or alternatively the thickness of the nozzle 20 adjacent the weakened portion 28 must be configured such that the syringe 10 has sufficient strength to avoid breakage during heavy usage and handling.

A plunger 30 may be inserted within the syringe barrel 12. The plunger 30 may include a thumb or finger rest 32 and a plunger seal 34. The plunger 30 is used to move a treatment solution from within the syringe barrel 12 and through the nozzle 20.

A needle assembly 36 may be coupled to the nozzle 20 at the nozzle distal end 24 using a needle hub 42. Preferably, the needle assembly 36 comprises a proximal needle end 38 and a distal needle end or tip 40 as is conventionally known. The proximal needle end 38 is coupled to the needle hub 42 using conventional means and methods as previously described.

The needle hub 42 has a proximal needle hub end 44 which may be connected with the nozzle 20 at the distal end 16 of the syringe. This connection may comprise a slip-type coupling wherein the needle hub 42 has an internal cavity within the proximal end 44 of the needle hub 42. The nozzle distal end 24 is insertable within the cavity of the hub 42, as is conventionally known. This connection may include a slip fit, a spin weld or any other means or method of conventionally attaching the needle hub 42 to the nozzle 20. Alternatively, the needle hub 42 may be permanently coupled to the nozzle distal end 24 and formed as an integral part of the syringe 10. For example, the needle hub 42 may be molded as part of the nozzle 20.

The proximal needle hub end 44 preferably comprises a flat surface 46 and preferably, this flat surface 46 is generally perpendicular to the longitudinal axis 18. The needle hub 42 includes a hub passageway which is configured to be aligned with the syringe passageway 26 when coupled with the nozzle 20. The needle hub passageway is also aligned with and fluidly connected with the proximal needle end 38 to allow the treatment fluid to pass through the needle assembly 36.

The weakened portion 28 may be located about the nozzle 20 proximally to a connection point 48 defined by the junction of the proximal needle hub end 44 and the nozzle 20. Preferably, the weakened point 28 may be located on the nozzle 20 adjacent this connection point 48. This connection point 48 may even be configured as the weakened portion 28.

In the present invention, the term "syringe" is intended to comprehend and include conventional syringes as well as other intravenous needle devices. Particularly, the term "syringe" is intended to include syringes, accesses and stylets. These syringes include blood collection syringes, intramuscular as well as other syringes which are connectable to an intravenous needle assembly. Accesses and stylets include intravenous devices having a nozzle or hub portion and which may be coupled to a needle assembly and used as an intravenous port or access. Also, the term "needle" and "needle assembly" are intended to comprehend hypodermic needles, including blood-drawing needles, intramuscular needles as well any other injection needle.

Figure 2:
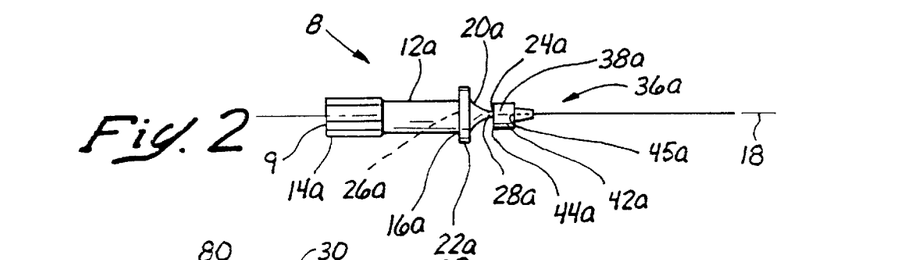
FIG. 2 is an alternative embodiment of a syringe according to the principles of the present invention shown coupled with a needle assembly.

Referring now to FIG. 2, an alternative embodiment of a syringe 8 constructed in accordance with the principles of the present invention is shown. In this embodiment, like features to those of the previous embodiment are designated by like reference numeral succeeded by the letter "a". The syringe 8, which may be an intravenous needle assembly such as an access or stylet, includes a barrel 12a which extends from a proximal end 14a to a distal end 16a along a longitudinal axis 18a.

A nozzle 20a having a proximal nozzle end 22a tapering into a distal nozzle end 24a, or similar shaped portion, may be connected or otherwise coupled to the distal end 16a of the barrel 16a. Preferably, the proximal nozzle end 22a includes a flange 23 which is directly coupled to the distal end 16a. A hub 42a may be coupled to the distal nozzle end 24a and includes a proximal hub end 44a and a distal hub end 45a. Preferably, the nozzle 20a and the hub 42a are constructed as an integral part of the syringe 8 and may form a single molded piece. A plug 9 may be incorporated into the proximal end of the barrel 12a.

A needle assembly 36a may be attached to the hub 42a. Preferably, the needle assembly 36a is an integral part of the hub 42a, which in turn is integral to the syringe 8 as previously described. However, the needle assembly 36a may be removably attached to the hub 42a. A weakened portion 28a is incorporated into the nozzle portion 20a. Preferably, the weakened portion 28a is disposed adjacent the distal nozzle end 24a and adjacent the proximal hub end 44a. The weakened portion 28a allows the syringe 8 to be broken similarly to that previously described. Preferably, the weakened portion 28a is oriented on the syringe 8 just proximally from a proximal needle end 38a.

Figure 3:
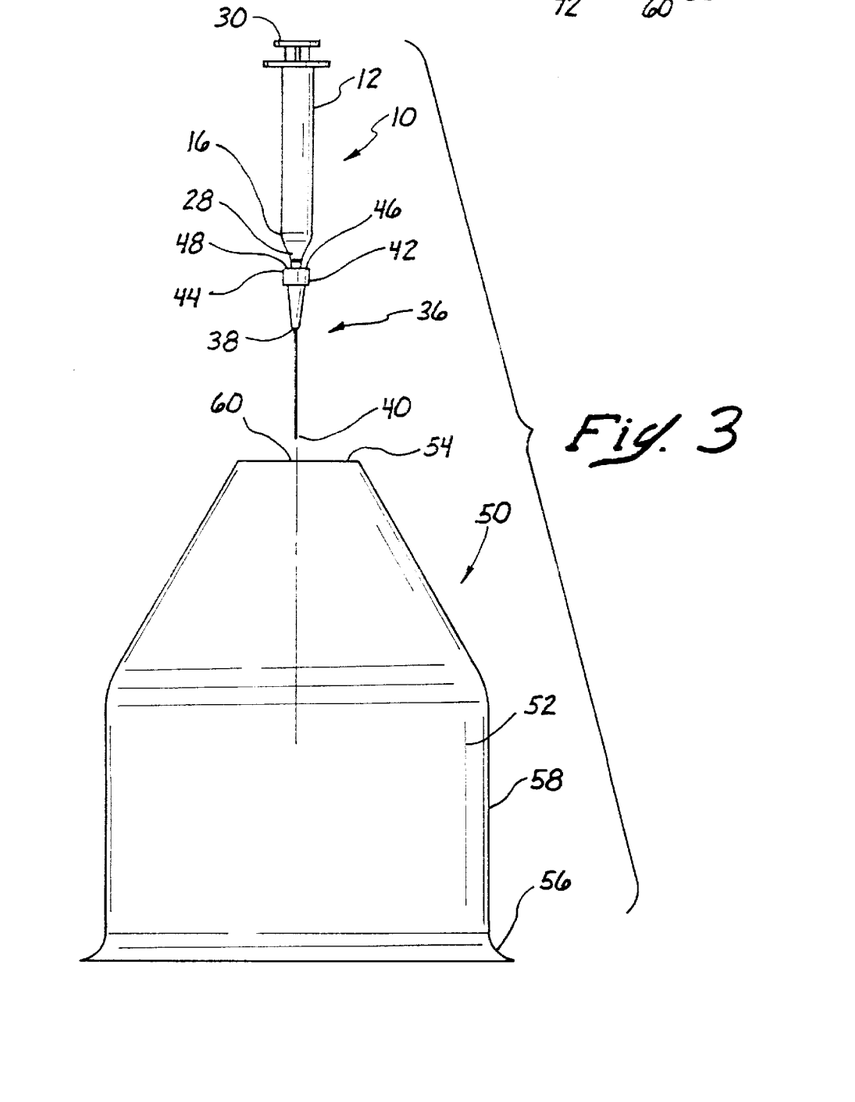
FIG. 3 is a side elevational view of the syringe and needle assembly of FIG. 1 shown being inserted into a disposal apparatus according to the present invention.

Referring now to FIG. 3, an embodiment of a disposal apparatus 50 for use in breaking and disposing of the syringe 10 and needle assembly 36 will be described. The disposal apparatus 50 generally includes an open enclosure or container body 52 and an attached top or upper portion 54. The container body 52 preferably includes a base 56 and a surrounding sidewall 58. Preferably, the sidewall 58 is continuous around the base 56 and may be in most any shape. The base 56, the sidewall 58 and the upper portion 54 may each comprise a plastic, a metal or any other material which cannot generally be penetrated by hypodermic needles or reacts to medical fluids and waste products. Additionally, the base 56 is preferably configured to resist overturning or movement during use. Thus, the base 56 may be configured with a large surface area, including a non skid base, for contact with a supporting surface.

The upper portion 54, which may be removably connected to the container body 52, includes an aperture 60 configured for receiving the nozzle portion 20 of the syringe 10, including the attached needle hub 42 and needle assembly 36. The aperture 60 includes a generally rigid and surrounding aperture wall 62. Preferably, this aperture wall 62 is oriented on the inner side of the upper portion 54 within the container body 52.

The aperture 60 and surrounding aperture wall 62 are preferably sized with a diameter slightly larger than the maximum diameter of the needle hub 42. This allows the needle hub 42 and the needle assembly 36 to freely be inserted into the aperture 60 but restricts the entrance of anything of larger diameter, such as the syringe barrel 12. If the syringe barrel 12 has a diameter equal to or smaller than that of the aperture 60, a mechanical stop may be provided to ensure it can not enter the aperture 60. Thus, the needle hub 42 and the needle assembly 36 may be mechanically restrained from passing too far within the aperture 60 by the larger diameter syringe barrel 12 or alternatively by a mechanical stop on the syringe barrel 12 or even on the upper portion 54 of the disposal container 50. The aperture 60 and aperture wall 62 are configured to generally rigidly support the syringe 10 and coupled needle assembly 36 once the needle assembly 36 is fully inserted into the aperture 60.

A one-way device or locking mechanism 62 may be coupled to the upper portion 54. Alternatively, the locking mechanism 64 may be coupled to the container body 52. The locking mechanism 64 may include a locking tip 66 which is movable within the aperture 60 to engage the needle hub 42 and needle assembly 36 and prevent their removal from within the aperture 60. Preferably, the locking mechanism 64 includes a flexible or otherwise movable arm 68 which is coupled to the upper portion 54 at a first end 70 and to the locking tip 66 at a second end 74.

More specifically, the locking tip 66 may be configured with an upper or proximal side which includes a tapered edge that generally faces the aperture 60 and allows the needle hub 42 and the assembly 36 to easily slide into the aperture 60. The locking tip 66 may also include a lower or distal side which includes a flat surface or ledge which generally faces the base 56. The tapered upper side and the flat or locking lower side are configured such that they fit between the needle hub 42 and the nozzle 20. The locking tip 66 may be moved over to engage the flat surface 46 on the needle hub 42. This engagement prevents the needle hub 42 and the attached needle assembly 36 from being pulled out or otherwise withdrawn from within the aperture 60 and the disposal container 50.

Referring now to FIGS. 1 through 6, insertion of the syringe 10 into the disposal apparatus 50 and the general action of the locking mechanism 64 will be described in further detail. When a syringe 10, and particularly a syringe 10 having a needle hub 42 and needle assembly 36 attached as generally shown in FIGS. 1 & 2 and described herein, requires disposal, the disposal apparatus 50 may preferably be utilized. In particular, the needle distal end or tip 40 may be first inserted into the aperture 60, as illustrated in FIG. 3. Preferably, this insertion is generally along a path longitudinal with the center of the aperture 60 and is guided by the rigid aperture wall 62 once penetration is commenced. As mentioned, the aperture 60 is configured such that the aperture wall 62 defines a diameter which is slightly larger than the outer diameter of the attached needle hub 42. In this way, the needle hub 42 may be held relatively securely within the aperture 60. This configuration may require a specific aperture 60 for each needle hub 42 diameter utilized. Thus, differing syringes 10 and particularly, differing sized needle hubs 42, may require different apertures 60 within the disposal apparatus 50. However, it is envisioned that various types and sizes of syringes 10 may be made, according to the principles of the present invention, which utilize similar sized needle hubs 42, reducing or even eliminating the need for multiple apertures 60.

The syringe 10 may be further inserted within the aperture 60 until the locking mechanism 64 engages the proximal needle hub end 44. More specifically, during insertion of the needle assembly 36 and the attached needle hub 42, the locking tip may be maintained against the needle hub 42 as it is inserted into the aperture 60 through the flexible arm 68. In particular, the locking tip 66 slides along the needle hub 42 until the proximal needle hub end 44 is inserted within the aperture 60 beyond the lower side of the locking tip 66. This allows the lower side of the locking tip 66 which has a flat surface to move over the flat surface 46 of the proximal needle hub end 44. Once the locking tip 66 has engaged the flat surface 46 of the needle hub 42, the needle assembly 36 and the attached syringe 10 can not be removed from within the aperture 60. As mentioned, the larger diameter syringe barrel 12 or alternatively a mechanical stop may be used to prevent the syringe 10 and attached needle hub 42 and needle assembly 36 from entering further into the disposal container 50.

It is important to understand that various other apparatus and method may be used to prevent the removal of the syringe 10, needle hub 42 and attached needle assembly 36 once inserted within the aperture 60. For example, the locking tip 66 may be slidably disposed within the container body 50. A biasing spring or similar device may be used to maintain the locking tip 66 within the aperture 60 while allowing the needle assembly 36 to be inserted therethrough. A number of flexible rings oriented downwardly in a Chevron fashion, may also be inserted within the aperture 60. Once engaged within the needle hub 42 and particularly, the flat surface 46, these rings prevent the removal of the needle hub 42 and attached needle assembly 36. Any other method or apparatus may also be used which maintains the syringe 10, needle hub 42 and attached needle assembly 36 within the aperture 60 and prevents its removal.

A one-way door 74 may be provided within the disposal container 50 and more preferably adjacent the aperture 60. This one-way door 74 may be configured to open upon contact by the entering needle tip 40 and to remain open during entrance of the needle hub 42 and attached needle assembly 36. Preferably, the one-way door 74 closes upon the removal of the needle hub and attached needle assembly 36 from within the aperture 60, such as after being broken away from the syringe 10 and freely falling inside the disposal apparatus 50. This door 74 closure prevents the penetration of any needle assemblies 36 retained within the container body 50. Thus, the one-way door 74 should be made from a material which provides a generally frictionless surface when poked with a needle assembly 36. The one-way door 74 may be pivotally coupled to the upper portion 54 and biased to close against the aperture 60 using a spring 76 or other similar device. A seal 78 may be disposed between the one-way door 74 and the aperture 60 to prevent the escape of any fluid or gas from within the disposal apparatus 50.

Figures 5, 6, 7:
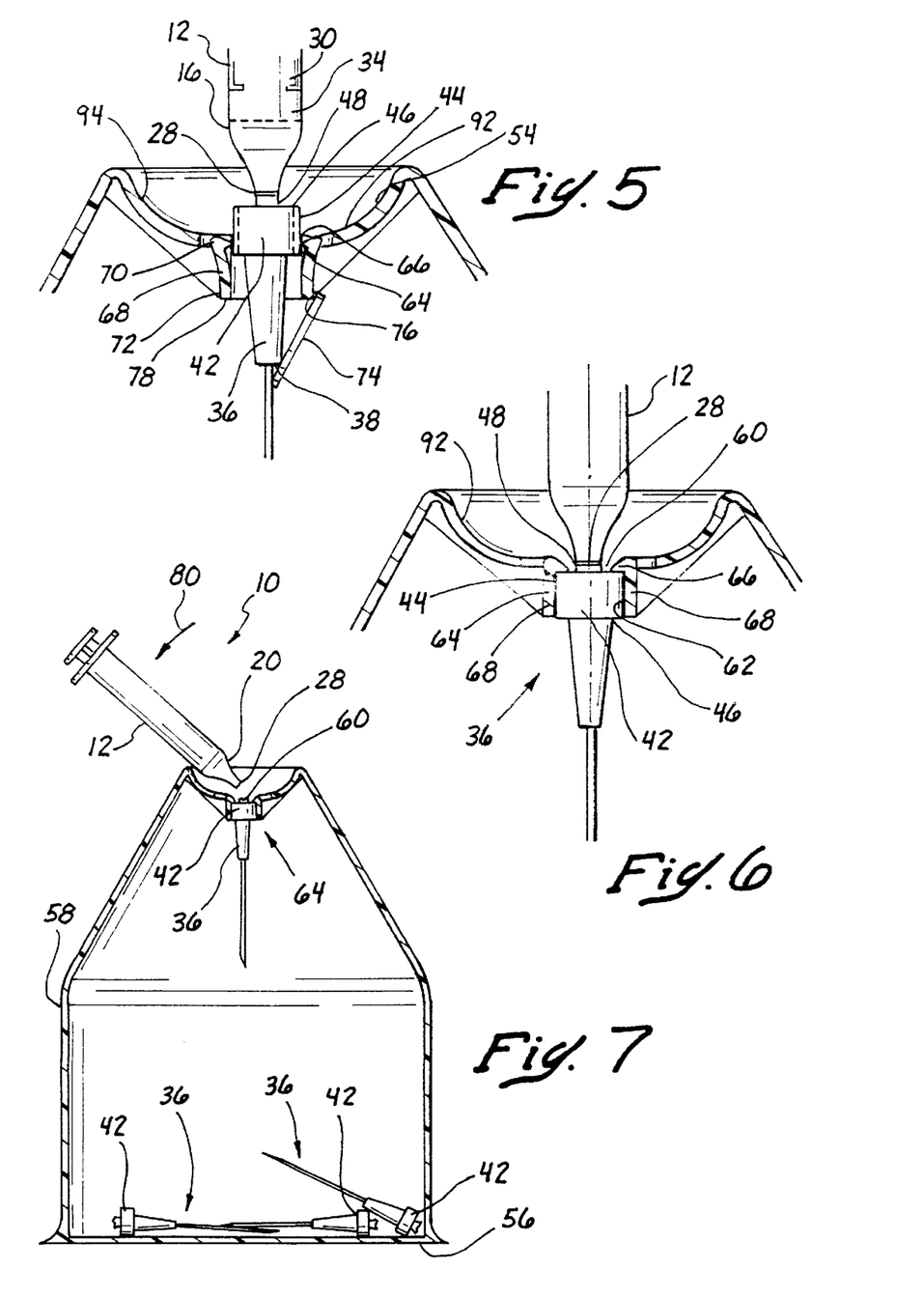
FIG. 5 is an enlarged partial view of the syringe and needle assembly of FIG. 1 shown being inserted into the disposal apparatus shown in FIG. 3.
FIG. 6 is an enlarged partial view of FIG. 4 indicated along line 6.
FIG. 7 is a cross-sectional view of FIG. 4 showing the syringe being broken away from needle assembly within the disposal apparatus.

Once the syringe 10, needle hub 42 and attached needle assembly 36 have been inserted into the aperture 60 within the disposal apparatus or container 50, the syringe 10 may be broken across the weakened portion 28. As best illustrated in FIG. 7, movement of the syringe barrel 12 relative to the nozzle distal end 24 retained within the aperture 60 forces the syringe 10 to sever or break along the weakened portion 28. Preferably, a lateral force, indicated by the arrow 80, applied to the proximal barrel end 14, creates a bending force or moment along the syringe barrel 12 and nozzle 20. When a sufficient lateral force 80 is applied, the syringe 10 will break across the weakened portion 28 due to its weakened cross-section and smaller diameter. Once the nozzle distal end 24 and attached needle assembly 36 are broken away from the syringe barrel 12, they may freely drop within the container body 50. As previously mentioned, a one-way door 74 may be provided to close the aperture 60.

Figure 8:
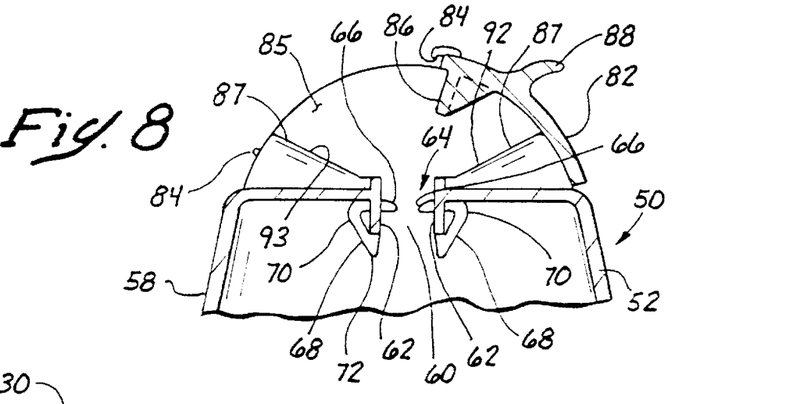
FIG. 8 is a partial cross-sectional view of the disposal apparatus of FIG. 4 shown having an embodiment of a movable cover according to the present invention.

Referring now to FIG. 8, a cover 82 may be movably mounted to the disposal apparatus 50 for covering at least some of the upper portion 54. The cover 82 may be used as a top or lid for covering the entire upper portion 54 but preferably covers at least the aperture 60. When the disposal apparatus 50 is provided with this cover 82, the need for a one-way door 74 as previously described, is minimized and may even be omitted.

The cover 82 is preferably configured such that it is movable between an open position and a closed position. In the open position, the aperture 60 is preferably open and exposed and a syringe 10 may be inserted therethrough. In the closed position, the aperture 60 is preferably covered and closed. The cover 82 may be provided with a seal or similar device to prevent and previously disposed needle hubs 42 and needle assemblies 36 from exiting through the aperture 60 as well as the escape of any fluids or gas. A spring or other biasing device may be used to maintain the cover 82 in a normally closed position. Alternatively, the cover 82 may be biased in the normally open position to facilitate use and lessen the need for a second operation step.

A lock or other securement device 84 may be provided to secure the cover 82 in the closed position. The lock 84 may be provided with a permanent connection such that once the disposal apparatus 50 is full or otherwise no longer necessary, the lock 84 may be activated and the cover 82 maintained in the closed position permanently. The lock 82 may include any device for retaining the cover 82 closed and secured to the container wall 58 or top 54.

When configured with a cover 82, the upper portion 54 is preferably configured with a pair of parallel side walls 85 which extend generally across the upper portion 54 and upwardly from the aperture 60. Preferably, each side wall 85 defines a semi circular shape (half round) and is disposed on either side of the aperture 60. Each semi cylindrical side wall 85 is disposed such that the highest position is located over the aperture 60. A tapered support surface 87 may be located between the side walls 85 on either side of the aperture 60. Preferably, the tapered support surfaces 87 taper downwardly and into the aperture 60. One of the tapered support surfaces 87 may be a very steep taper or even a cross wall between the opposing side walls 85.

The cover 82, which may be a generally u-shaped member having a triangular side configuration, may be pivotally connected to each of the side walls 85. Preferably, each of the triangular legs of the u-shaped cover 82 extends over one of the side walls 85. The cover 82 is configured to pivot over the aperture 60 from the open position to the closed position.

The cover 82 may be configured with a syringe contact ledge 86 to assist in contacting and applying a lateral force 80 to the syringe barrel 12 and to facilitate the breakage of the syringe 10 along the weakened portion 28. As discussed, the cover 82 is preferably pivotally mounted to either the container body 50 or the upper portion 54 and more preferably, to the side walls 85, such that it may be pivoted between the open position and the closed position. In the open position, the cover 82 allows a syringe, such as the syringe 10 previously described, to be inserted between the side walls 85 and into the aperture 60 as previously described. The tapered surfaces 87 may facilitate directing the needle assembly 36 into the aperture 60. As the cover 82 is pivoted to the closed position, the syringe contact ledge 86 contacts the proximal barrel end 14. Preferably, this syringe contact ledge 86 is configured to contact the proximal barrel end 14 and maximize the bending force applied while minimizing the effort to pivot the cover 82 and break the syringe 10. Further movement of the cover 82 towards the closed position acts to break the syringe 10 about the weakened portion 28.

The cover 82 may be configured with a hand or finger grip 88. This grip 88 provides a protective shield against the splatter of any fluid or gas within either the container 50 or the syringe 10. Additionally, the grip 88 may provide a leverage arm facilitating breaking or severance of the syringe 10.

Figure 9:
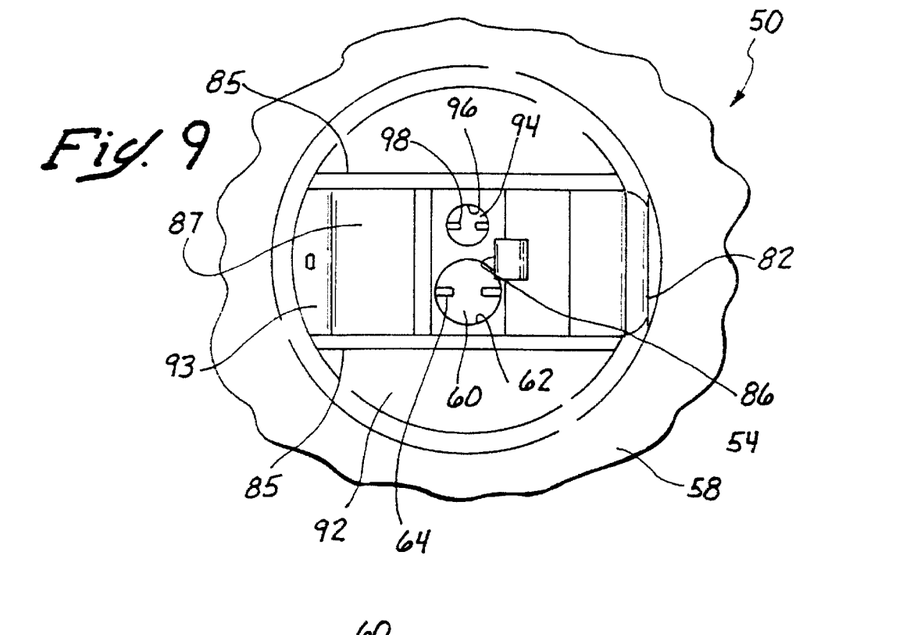
FIG. 9 is a cross-sectional view of an alternative embodiment of a disposal apparatus according to the present invention.
Figure 10:
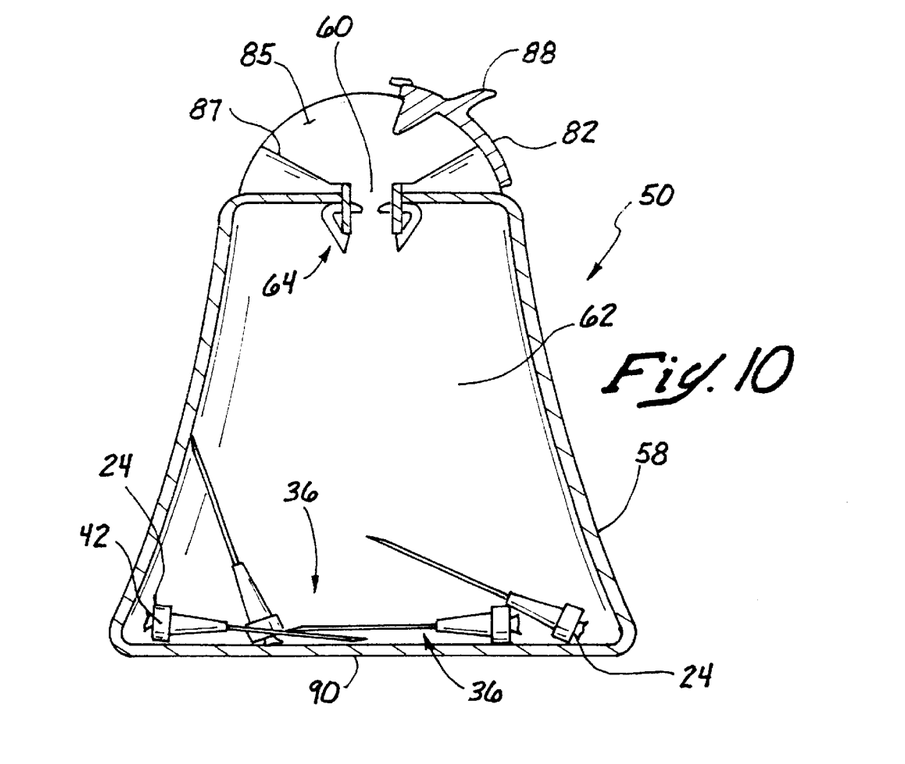
FIG. 10 is a top view of the disposal apparatus of FIG. 9.

Referring now to FIGS. 9 and 10, in combination with FIGS. 3 through 8, the container body 50 may be configured in most any shape. As illustrated in FIG. 10, the container body 50 includes a continuous sidewall 58 which tapers outwardly and downwardly into the base 56. This configuration provides a stable disposal apparatus 50 which resists overturning moments as well as premature breakage of the syringe 10 due to disposal apparatus 50 movement during disposal. A base pad 90 or other anti-skid/slip device may be provided on the underside of the base 56 for contacting and preventing movement against any surface on which the disposal apparatus 50 may be placed. In a preferred embodiment, the container body 52 has a shape and size which facilitates gripping in an upright position by an average sized human hand. The container body 52 and even the sidewall 58 may be provided with a handle or mounting device for holding or securing the apparatus 50 during use.

The top or upper portion 54 may also be configured in a variety of different shapes and sizes. For example, the upper portion 54 may include a generally continuous surface 92 which is concave and smoothly tapers inwardly into the aperture 60. Alternatively, the surface 92 may define a small outer lip around the aperture 60. These configurations may be advantageous as they may better direct the needle assembly 36 along with the attached hub 42 and syringe 10 into the aperture 60. In addition, the tapered surface 92 may be configured to support the syringe barrel 12 once broken and retain it from falling off of the upper portion 54. Additionally, a tapered surface 92 directs any spilled liquid from within the syringe 10 into the aperture 60 for disposal within the container body 50. Thus, the aperture 60 is preferably disposed at a lowermost position on the surface 92 of the upper portion 54. In effect, the tapered surface 92 provides a protective shield around the aperture 60.

The upper portion 54 may also be specifically provided with a support ledge 93 for supporting and retaining the syringe barrel 12 after it has been broken away from the needle hub 42. This support ledge may be the tapered surface 87 as previously described or a more specifically configured surface. The support ledge 93 may be aligned with the cover 82 such that the broken off syringe barrel 12 is captured between the contact ledge 86, the opposing side walls 85 and the support ledge 93. To facilitate this capture, either or both of the contact and support ledge 86 and 93 may be configured with a curved surface which generally mates with the surface of the syringe barrel 12.

The disposal apparatus 50, and particularly the upper portion 54 may comprise a number of apertures for receiving multiple and possibly different sized and types of syringe and needle assemblies. As shown in FIG. 9, and best illustrated in FIG. 10, a second aperture 94 having a second aperture wall 96 and a second locking mechanism 98 may be provided within the upper portion 54 and configured to receive a second syringe and needle assembly. The second aperture 94 may be configured to function substantially similar to the aperture 60 previously described. Preferably, the second aperture 94 is aligned between the side walls 85 and generally perpendicular to the side walls 85.

The second syringe and needle assembly may be configured substantially like the syringe 10, needle hub 42 and needle assembly 36 previously described, but may be of a different size or overall shape. The second aperture 94 within the disposal apparatus 50 allows for the breaking and disposal of two different syringe and needle assemblies within one disposal container 50. In particular, the first aperture 60 may be used for disposal of a first type of syringe, such as syringe 10 and the second aperture 94 may be used for disposal of a second type of syringe, such as syringe 8.

Referring now back to FIGS. 1 through 10, a method for breaking and disposing of a syringe 10 having an attached needle nub 42 and needle assembly 36 will be described. The method includes the step of providing a syringe 10 having a syringe barrel 12 and an attached nozzle 20 with a weakened portion 28 adjacent a nozzle distal end 24, as previously described. A needle assembly 36 having a proximal needle end 44 and a needle tip at a distal needle end 40 may be generally coupled to a needle hub 42 as previously described. The needle hub 42 may in turn be coupled to the nozzle distal end 24 distally of the weakened portion 28 using conventional means or methods and as also previously described.

In order to break the syringe 10 and coupled needle hub 42 and needle assembly 36, the method includes the step of holding or maintaining the combined assembly 10, 42 & 36 such that the needle hub 42 and associated needle assembly 36 are maintained in a relatively fixed position relative to the syringe barrel 12. The syringe barrel 12 may then be moved relative to the relatively fixed needle hub 42 such that the syringe barrel 12 is broken away from the needle assembly 36 about the weakened portion 28.

The step of moving the syringe barrel 12 relative to the needle hub 42 may include moving the proximal barrel end 14 or adjacent portion of the syringe 10 laterally relative to the more rigidly held needle hub 42 until the syringe 10 actually breaks about the weakened portion 28. However, the step of moving may include any form of bending the syringe barrel 12 relative to the nozzle distal end 24 or needle hub 42 such that the syringe barrel 12 is broken about the weakened portion 34. Twisting of the syringe barrel 12 may also be utilized but may require the holding the needle hub 42 from rotating.

The method may also include the step of providing a disposal apparatus or container 50 to facilitate the breaking and disposal of the needle assembly 36, the attached needle hub 42 and the portion of the nozzle 20 which is distal of the weakened portion 28. The disposal container 50 preferably includes a top or upper portion 54 having an aperture 60 leading into a container body 52 for receiving and supporting the needle assembly 36 and more specifically, the needle hub 42 and any attached needle assembly 36.

Figure 4:
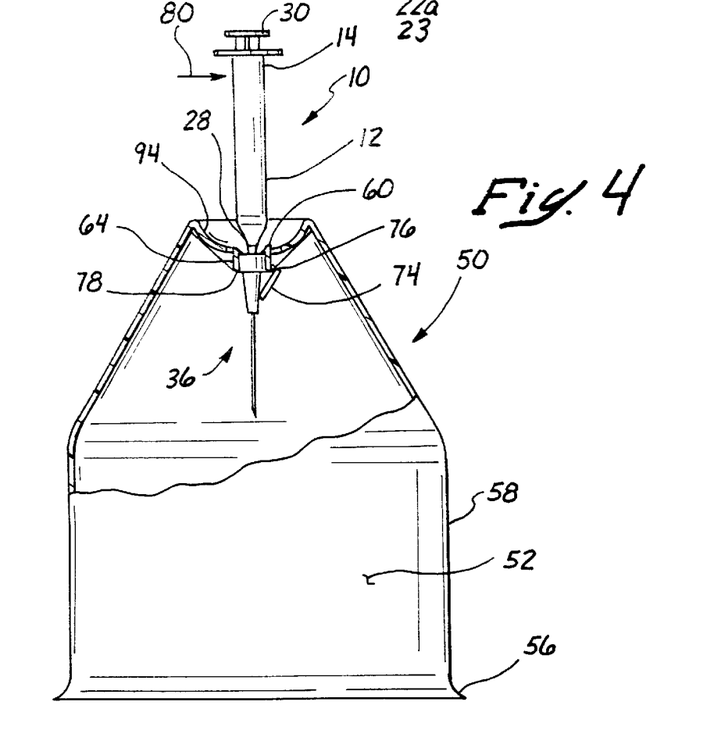
FIG. 4 is a cross-sectional view of the syringe and needle assembly of FIG. 1 shown inserted into the disposal apparatus of FIG. 3.

The syringe 10 and particularly, the attached needle hub 42 and needle assembly 36 may then be inserted into the aperture 60 within the upper portion 54 of the container 50, as best illustrated in FIGS. 3 and 4. After inserting the needle assembly 36 into the aperture 60, the needle hub 42 may be inserted and also engaged within the aperture 60 such that the needle hub 42 is supported and generally rigidly held by the aperture wall 62 within the upper portion 54 of the disposal container 50. The syringe barrel 12 and the nozzle distal end 24 may then be broken about the weakened portion 28 as previously described. The broken off needle assembly 36, needle hub 42 and nozzle distal end 24 are now free to fall into the disposal container 50. The remaining portion of the syringe 10, including the syringe barrel 12 and nozzle proximal end 22, may then be removed from the upper portion 54 of the container 50.

The method may also include the step of moving an actuator or cover 82 which is movably attached to the upper portion 54 of the container 50 such that a syringe contact ledge 86, contacts the syringe barrel 12 and forces the syringe barrel 12 to move laterally relative to the generally rigidly held needle hub 42. The cover 82 is moved until the nozzle 20 breaks about the weakened portion 28.

It will be understood that various modifications can be made to the various embodiments of the present invention herein disclosed without departing from the spirit and scope thereof. For example, various sizes of the breakaway syringe and the disposal apparatus are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present as defined by the claims appended hereto.

What is claimed is:

1. An apparatus adapted for use with a syringe having a body including a barrel and a nozzle, and an attached needle assembly including a hub and a needle, and said apparatus comprising:
    a container having a base and at least one side wall, said container body adapted to contain said needle hub needle assembly and a portion of said syringe body;
    an upper portion of said container, said upper portion having an aperture for receiving at least said needle hub, said aperture having a generally rigid aperture wall for supporting the needle hub and attached syringe body;
    a locking mechanism having a locking tip moveable within the aperture for engaging the needle hub and preventing the removal of the needle hub from the container; wherein
    the needle hub is held in a generally fixed relationship with the aperture of the container, permitting lateral movement of the syringe to facilitate breaking the syringe at the weakened portion.

2. The apparatus as recited in claim 1, and further comprising a one-way door biased from an open position to receive the needle hub toward a closed position to seal the aperture.

3. The apparatus as recited in claim 1 wherein the locking mechanism comprises a flexible arm connected to the upper portion at a first end and to the locking tip at a second end.

4. The apparatus as recited in claim 1 wherein said upper portion is removably connected to said container body.

5. The apparatus as recited in claim 1 wherein the container is formed of a plastic.

6. The apparatus as recited in claim 1 wherein the upper portion of said container comprises a concave surface and said aperture is positioned at a lowermost position of said concave surface.

7. The apparatus as recited in claim 1, further comprising a second aperture in the upper portion sized and configured to receive a second syringe, said second aperture having a second locking mechanism for retaining a portion of said second syringe to facilitate breaking the second syringe.

8. The apparatus as recited in claim 1, and further comprising a cover for covering at least a portion of said aperture.

9. The apparatus as recited in claim 8 wherein the cover comprises a syringe contact ledge and wherein the cover is movably coupled to one of the container body and the upper portion, said cover for covering the aperture and said syringe contact ledge for use in bending the syringe barrel relative to the nozzle.

10. The apparatus as recited in claim 9 wherein the upper portion comprises a support ledge for supporting and retaining the syringe barrel after being broken from the nozzle retained within the aperture.

11. A method for breaking a syringe having an attached needle hub and needle assembly such that the needle hub and needle assembly are broken away from the syringe, the needle assembly having a needle tip at a distal needle end attached to said needle hub at a proximal needle end, the method comprising the steps of:
    providing a syringe having a syringe barrel and a nozzle coupled to a needle hub, said nozzle having a weakened portion adjacent said needle hub;
    maintaining the needle hub in a substantially fixed position relative to the syringe barrel;
    during the maintaining step, inserting at least the needle hub into a multi-needle container; and
    moving the syringe barrel relative to the container to break the syringe at the weakened portion of the nozzle.

12. The method as recited in claim 11 wherein the step of moving comprises moving the syringe barrel laterally relative to the needle hub until the syringe and needle assembly breaks.

13. The method as recited in claim 11 wherein the moving step further comprises bending the syringe and needle assembly such that the syringe barrel is bent relative to the needle hub until the syringe barrel is broken away from the needle assembly along the weakened portion.

14. The method as recited in claim 11 wherein the step of maintaining comprises:
    providing the container with an enclosing upper portion having an aperture for receiving and retaining the needle hub, the aperture having a rigid aperture wall defining an opening into the container;
    inserting the needle assembly into the aperture; and
    engaging the needle hub within the rigid aperture wall such that the needle hub is retained in the substantially fixed position relative to the container.

15. The method as recited in claim 14 wherein the step of moving comprises:
    moving the syringe barrel at relative to the container such that the needle assembly, the needle hub and a distal portion of the nozzle are broken away from said syringe barrel the weakened portion; and
    removing the syringe barrel from said container.

16. The method as recited in claim 14 wherein the step of moving comprises moving a cover pivotally attached to the container such that a portion of the cover contacts the syringe barrel forcing the syringe to break at the weakened portion.

17. The method as recited in claim 14 wherein the step of providing a container further comprises providing a container for removing and disposing the needle hub, the container having an upper portion with an aperture opening into the container and a locking mechanism for retaining the needle hub within the aperture and preventing the removal of the needle hub from within the aperture and wherein the inserting and engaging steps comprise inserting the needle assembly into the aperture until the locking mechanism engages the needle hub.

18. A disposal apparatus adapted for use with a syringe having a body and a needle assembly comprising:
    a base for supporting the apparatus on a convenient surface;
    at least one side wall forming with the base a container having a converging portion defining an aperture into the container, the aperture being sized and configured to receive at least the needle assembly into the container;
    an engagement mechanism disposed relative to the aperture and having properties for facilitating movement of the needle assembly inwardly of the container while inhibiting movement of the needle assembly outwardly of the container; and
    the engagement apparatus facilitating fracture of the syringe to permit separation of the needle assembly from at least a portion of the body to safely store the needle apparatus in the container.

19. The disposal apparatus recited in claim 18 wherein the needle assembly of the syringe includes a hub and a needle, and a disposal apparatus further comprises:

at least one arm bendable between the first position permitting movement of the needle and the hub into the container, and a second position prohibiting movement of the hub outwardly of the container.

20. The disposal apparatus recited in claim 19 wherein the arm is a first arm and the disposal apparatus further comprises a second arm disposed in opposing relationship to the first arm.

21. The disposal apparatus recited in claim 19 wherein the arm includes an inclined surface adapted to convert axial movement of the syringe into radial movement of the arm to the first position thereby facilitating movement of the needle assembly into the container.

22. The disposal apparatus recited in claim 18 further comprising a top wall configured to funnel the syringe toward the engagement mechanism.

23. The disposal apparatus recited in claim 22 further comprising a spring-biased door pivotally mounted to cover the aperture when the syringe is not present in the aperture.

* * * * *